(12) United States Patent
Shah (10) Patent No.: US 7,713,693 B1
(45) Date of Patent: May 11, 2010

(54) HUMAN CANCER CELL SPECIFIC GENE TRANSCRIPT

(75) Inventor: Girish Shah, Monroe, LA (US)

(73) Assignee: University of Louisiana at Monroe, Monroe, LA (US)

( * ) Notice: Subject to any disclaimer, the term of this patent is extended or adjusted under 35 U.S.C. 154(b) by 0 days.

(21) Appl. No.: 11/207,697

(22) Filed: Aug. 22, 2005

Related U.S. Application Data (60) Provisional application No. 60/606,477, filed on Sep. 1, 2004.

(51) Int. Cl.
*C12Q 1/68* (2006.01)
*G01N 33/53* (2006.01)

(52) U.S. Cl. ............................................ 435/6; 435/7.1
(58) Field of Classification Search ...................... 435/6, 435/7.1
See application file for complete search history.

(56) References Cited

U.S. PATENT DOCUMENTS

| 6,238,877 | B1 | 5/2001 | Wu et al. |
|---|---|---|---|
| 6,267,960 | B1 | 7/2001 | Reiter et al. |
| 6,369,195 | B1 | 4/2002 | An et al. |
| 6,465,181 | B2 | 10/2002 | Billing Medel et al. |
| 6,541,212 | B2 | 4/2003 | Reiter et al. |
| 6,613,510 | B2 | 9/2003 | Jenkins et al. |
| 6,649,163 | B1 | 11/2003 | Bander |
| 6,673,914 | B1 | 1/2004 | Hoon |
| 6,703,204 | B1 | 3/2004 | Mutter et al. |
| 6,720,138 | B2 | 4/2004 | Sharma et al. |
| 6,756,036 | B2 | 6/2004 | Reiter et al. |

OTHER PUBLICATIONS

Tockman et al (Cancer Res., 1992, 52:2711s-2718s).*
Gura (Science, 1997, 278:1041-1042.).*

* cited by examiner

*Primary Examiner*—Sean E Aeder
(74) *Attorney, Agent, or Firm*—Jones,Walker, Waechter, Poilevent, Carrere & Denegre, L.L.P.

(57) ABSTRACT

Disclosed are nucleic acid and amino acid sequences encoded by a novel Neuroendocrine-like marker (NELM) and diagnostic techniques for the detection of human prostate cancer utilizing such nucleic acid and amino acid sequences. Genetic probes and methods useful in monitoring the progression, diagnosis, and response to therapy of prostate cancer, as well as identifying compounds that promote prostate cancer are described.

3 Claims, 6 Drawing Sheets

Figure 1

Sense NELM (100X)

Fig. 2

Antisense NELM(100X)

A. Non-malignant (100X)

Fig. 4

B. Malignant(100X)

BPH 400X

Fig. 6

High-grade PIN +mod. Grade

Fig. 6a

High-grade PIN 400 X

Fig. 6b

Low grade 100X
Fig. 6c

Low grade 200X
Fig. 6d

Moderate grade 100X
Fig. 6e

Moderate grade 400X
Fig. 6f

Moderate grade 100X
Fig. 6g

Moderate grade 400X
Fig. 6h

A. Tonsils (400X)

Fig. 7

B. Lymph node (400X)

Fig. 7a

C. Liver (400X)

```
                              SEQUENCE LISTING

<160> NUMBER OF SEQ ID NOS: 1

<210> SEQ ID NO 1
<211> LENGTH: 132bp
<212> TYPE: DNA
<213> ORGANISM: Homo sapiens
<220> FEATURE:
<221> NAME/KEY:
<222> LOCATION:
<300> PUBLICATION INFORMATION:
<301> AUTHORS: NA
<302> TITLE: NA
<308> DATABASE ACCESSION NUMBER: NT029419NCBI

<400> SEQUENCE: 1
ggggtttctc catgttggtc aggctggtct cgaactccct caggtgatct              50
gcctgcctca gcctcccaaa gtgctgggat tacaggcgtg agccaccatg             100
cccggcaaca gtgtgtttca aaaagcagtt ta                                132
```

HUMAN CANCER CELL SPECIFIC GENE TRANSCRIPT

This invention relates to my provisional application 60/606,477 filed Sep. 1, 2004.

1. FIELD OF THE INVENTION

This invention relates generally to a cloned human cancer cell-specific gene transcript and more particularly to a Neuroendocrine-like Marker (NELM) useful in the noninvasive detection and monitoring of cancers. More particularly, the present invention concerns the production of probes and tools that would be useful in diagnosing, identifying, monitoring, and treating the progression of human prostate disease.

2. GENERAL BACKGROUND

Prostate cancer (PC) is a prominent cause of death in men in the United States (Boring et al., 1993; Wingo et. al., 1997). The development of diagnostic methods for this disease has demonstrated that it is one of the most prevalent of all cancers (Carter and Coffey, 1990). Although prostate cancer is the most common cancer found in United States men, the molecular changes underlying its genesis and progression remain poorly understood (Boring et al., 1993). The cancer statistics for the year 2004 predicts 230,110 new cases and 29,900 deaths from PC (Jemal et al, 2004). Significant advances have been made in the detection of PC over the last decade, which has been largely associated with the widespread use of prostate-specific antigen (PSA) screening. As a result, a dramatic increase in the incidents of PCs have occurred in the late 1980s and early 1990s, followed by a more recent fall in the incidence (Jemal et al, 2004)].

While prostate-specific antigen (PSA) screening has been useful in identifying PC patients in earlier stages of the disease, high PSA levels alone are not sufficient for the diagnosis of PC. In fact, recent evidence suggests that almost 20% of patients with "normal PSA" levels harbor prostate tumors, and a significant number of those are aggressive (Thompson et al, 2004). On the other hand, higher PSA levels are not sufficient proof for PC, as PSA levels rise in response to benign prostatic hyperplasia (BPH) as well as in response to increases in serum testosterone or prostate growth factors (Polascik et al, 1999). Specifically, serum PSA levels do not discriminate between the cases of BPH and PC (Catalona et al, 2000; Naya et al, 2003; Suzuki et al, 2004). This is because PSA protein is produced by normal as well as malignant prostate cells, and is not a cancer-specific protein, and serum PSA levels depend on the size of the prostate as well as serum testosterone levels. Therefore, the PSA test alone is not sufficient for PC diagnosis.

Numerous recent studies have identified several recurring genetic changes in prostate cancer including: allelic loss (Bova. et al., 1993; Macoska et al, 1994; Carter et al, 1990), generalized DNA hypermethylation, (Isaacs et al., 1994), point mutations or deletions of the retinoblastoma (Rb) and p53 genes (Bookstein et al., 1990a; Bookstein et al., 1990b; Isaacs et al., 1991), alterations in the level of certain adhesion molecules (Carter et al., 1990); Morton et al., 1993a; Morton et al., 1993b; Umbas et al., 1992), and aneuploidy and aneusomy of chromosomes (Macoska et al., 1994; Visakorpi et al., 1994; Takahashi et al., 1994; Alcaraz et al., 1994).

Commonly utilized current tests for prostate cancer are digital rectal examination (DRE) and analysis of serum prostate specific antigen (PSA). Although PSA has been widely used as a clinical marker of prostate cancer since 1988 (Partin and Oesterling, 1994), screening programs utilizing PSA alone or in combination with digital rectal examination have not been successful in improving the survival rate for men with prostate cancer (Partin and Oesterling, 1994). While PSA is specific to prostate tissue, it is produced by normal and benign as well as malignant prostatic epithelium, resulting in a high false-positive rate for prostate cancer detection (Partin and Oesterling, 1994).

Another serum marker associated with prostate disease is prostate specific membrane antigen (PSMA) (Horoszewicz et al., 1987; Carter et al., 1996; Murphy et al., 1996). PSMA is a Type II cell membrane protein and has been identified as Folic Acid Hydrolase (FAH) (Carter et al., 1996). Antibodies against PSMA react with both normal prostate tissue and prostate cancer tissue (Horoszewicz et al., 1987). Murphy et al. (1995) used ELISA to detect serum PSMA in advanced prostate cancer. As a serum test, PSMA levels are a relatively poor indicator of prostate cancer. However, PSMA may have utility in certain circumstances. PSMA is expressed in metastatic prostate tumor capillary beds (Silver et al., 1997) and is reported to be more abundant in the blood of metastatic cancer patients (Murphy et al., 1996). PSMA messenger RNA (mRNA) is down-regulated 8-10 fold in the LNCaP prostate cancer cell line after exposure to 5-alpha-dihydroxytestosterone (DHT) (Israeli et al., 1994).

There remains deficiencies in the art with respect to the identification of genes linked with the progression of prostate diseases, the development of diagnostic methods to monitor disease progression, and the development of therapeutics to treat prostate diseases and cancers. The identification of genes that are differentially expressed in prostate diseases would be of considerable importance in the development of a rapid, inexpensive method to diagnose prostate diseases, including cancer. The identified genes would also be useful in therapeutic compositions, or in screening assays for therapeutic compounds.

3. SUMMARY OF THE INVENTION

The present invention provides unique markers, that are shown herein to be useful in diagnosing or identifying a subject in all stages of prostate cancer, beginning with pre-malignant intraepithelial neoplasia (PIN) and ending with metastatic prostate cancer. The metastatic cancer markers of the present invention are shown to be absent or down regulated in a metastatic state, but are found in the prostate tissue or serum of subjects known not to have metastatic prostate cancer. The markers identified herein are shown to distinguish a condition of metastatic prostate cancer from a condition of normal (healthy), benign hyperplasia and confined prostate cancer. Diagnosis of the metastatic state, as disclosed herein, may include but is not limited to examination for the presence of specific markers in a prostate tissue sample, in a serum sample or both from subjects suspected of having a prostate disease. The ability to distinguish different stages of prostate disease has important implications for treatment or management of the subject's condition.

The identification of markers, or of differential expression of certain genes or gene products, in the practice of the invention may take any of several forms. For example, one may detect expression or lack of expression of an mRNA or other RNA product, or one may detect the expression or lack of expression of a protein or polypeptide in a certain cell, tissue or other biological sample of a subject. These RNA species and the corresponding encoded protein species have utility, for example, as markers of prostate disease state and as targets for therapeutic intervention in prostate disease.

The identified markers of prostate disease can in turn be used to design specific nucleic acid probes and primers, for example for the direct hybridization to a target mRNA or for use as primers in amplifying a target to be identified or quantified using an enzyme dependent amplification. When used in combination with nucleic acid molecule hybridization and amplification procedures, these probes and primers permit the rapid analysis of prostate biopsy core specimens, serum samples, etc. This will assist physicians in diagnosing prostate disease and metastatic prostate disease in particular, and in determining optimal treatment or disease management courses for individuals with various stages of prostate disease. The same probes and primers may also be used for in situ hybridization or in situ PCR detection and diagnosis of prostate disease.

The present invention may be described as a method of diagnosing a metastatic prostate disease state in a subject, comprising the steps of obtaining a test sample from prostate tissue, or serum, or both of said subject and detecting the up-regulation of a Neuroendocrine-like Marker (NELM). This can be accomplished by assessing the level of NELM mRNA or peptide products of the NELM mRNA in the epithelium of the prostate; in prostate tissues; in distant metastases; in serum or other biological fluids. Increased levels of one or more of the markers are then compared with levels found in non-cancerous samples. The increased level of detection indicates the presence of disease, with the extent of increase serving as an indication of the severity of the disease.

The NELM marker (SEQ ID NO:1) is a novel gene transcript from a human prostate cancer cDNA library. In the practice of this embodiment, one may use a nucleic acid segment that is complementary to the full length of the mRNA encoded by a marker gene, or one may use a smaller segment that is complementary to a portion of the marker RNA. Such smaller segments may be from about 14, about 15, about 16, about 17, about 18, about 19, about 20, about 21, about 22, about 23, about 24, about 25, about 25, about 30, about 50, about 75, about 100 or even several hundred bases in length and may be contained in larger segments that provide other functions such as promoters, restriction enzyme recognition sites, or other expression, or message processing, or replication functions. In preferred embodiments nucleic acid molecules are designed to selectively hybridize to the NELM-associated sequence DNA or mRNA or product thereof. A product thereof would include a DNA or RNA strand that is complementary to the mRNA and thus a useful probe would include both the sense and antisense orientations of a particular sequence. Such detection may be by any means known in the art and may include any nucleic acid hybridization measure method used for the direct detection of sample nucleic acids located in prepared patient and control samples, or in situ detection of sample nucleic acids located within the cells of the sample. The sample nucleic acids may also be separated from the cell prior to contact. The sample nucleic acids may be DNA or RNA.

The methods of the present invention may also include determining the amount of hybridized product. Such determination may be by direct detection of a labeled hybridized probe, such as by use of a radioactive, fluorescent or other tag on the probe, or it may be by use of an amplification of a target sequence, and quantification of the amplified product. A preferred method of amplification is a reverse transcriptase polymerase chain reaction (RT-PCR). RT-PCR is a preferred method of detection, diagnosis, and/or prognosis of prostate disease or cancer. In the practice of such a method, amplification may comprise contacting the marker ribonucleic acids with a pair of amplification primers designed to amplify the NELM mRNA, or even contacting the ribonucleic acids with a pair of amplification primers designed to amplify a nucleic acid segment comprising the nucleic acid sequence or complement of NELM.

In the practice of the invention, some methods may involve detection of expression of a polypeptide product of the marker gene. Such detection may be by any means known in the art and may include an immunoassay, immunoaffinity purification or detection, an ELISA, or a radioimmunoassay, for example.

The presence or amount of NELM may be determined by means of a molecular biological assay. Such molecular biological assays will often comprise a direct or indirect step that allows a determination of the sequence of at least a portion of the NELM nucleic acid sequence or another acceptable normal allelic or polymorphic sequence of NELM.

The methods may involve the use of isolated NELM nucleic acid segments, or synthetically produced nucleic acid sequences that bind to NELM sequences, that comprise a radioactive, enzymatic or fluorescent detectable label. The presence of NELM marker is established, and can be quantified, by measuring the amount of hybridized complementary nucleic acids in a sample by measuring or detecting the said label. In preferred embodiments such probes are designed to selectively hybridize to NELM mRNA or product thereof. A product thereof would include a DNA or RNA strand that is complementary to the mRNA and thus a useful probe would include both the sense and antisense orientations of a particular sequence. Also preferred are the use of probes or primers that are designed to selectively hybridize to a nucleic acid segment having a sequence of SEQ ID NO: 1 or the complements thereof.

The present invention may also be described in certain embodiments as a kit for use in detecting a metastatic prostate disease state through testing of a biological sample. A representative kit may comprise one or more nucleic acid segments as described above that selectively hybridize to NELM mRNA or its complement.

In certain embodiments, the kit for use in detecting a metastatic prostate disease state in a biological sample may comprise an antibody which immunoreacts with NELM nucleic acids or NELM-associated polypeptide products. Such an antibody may be a polyclonal antibody or a monoclonal antibody and may be included in a kit with reagents, secondary antibodies, labeling means, reaction vessels, or other components for product detection.

The invention further comprises the prognosis and/or diagnosis of prostate disease by measuring the amounts of NELM-associated products (nucleic acid and polypeptide products) formed as above. The amounts of products identified in an individual patient may be compared with groups of normal individuals or individuals with an identified disease state. Diagnosis may be accomplished by finding that the patient's levels of disease state markers fall within the normal range, or within the range observed in individuals with the disease state. Further comparison with groups of individuals of varying disease state progression, such as metastatic vs. non-metastatic cancer, may provide a prognosis for the individual patient. The invention further broadly comprises kits for performing the above-mentioned procedures.

Certain embodiments of the present invention comprise the use of antibodies specific to the proteins and peptides encoded by SEQ ID NO: 1. Such antibodies may be useful for diagnostic and prognostic applications in detecting the disease state, by comparing a patient's levels of NELM marker expression to expression of the same markers in normal or non-metastatic individuals. In certain embodiments, production of monoclonal or polyclonal antibodies can be induced by the use of the aforementioned nucleic acid sequences, proteins and peptides as antigens. Such antibodies may in turn be used to detect expressed nucleic acids or proteins as markers for human PC disease states. The levels of such antigens present in the peripheral blood, biological fluids, or prostate tissue sample of a patient may be quantified by conventional methods. Antibody-antigen binding may be detected and quantified by a variety of means known in the art, such as labeling antibody with fluorescent or radioactive labels and quantifying said labels. The invention further comprises kits for performing the above-mentioned procedures, wherein such kits contain antibodies specific for the aforementioned nucleic acids, proteins and peptides.

In one aspect, the present invention encompasses kits for use in detecting a prostate disease state in a biological sample. Such a kit may comprise one or more pairs of primers for amplifying nucleic acids corresponding to prostate disease marker genes. The kit may further comprise samples of total mRNA derived from tissue of subjects in various physiological states, such as normal, BPH, confined tumor and metastatically progressive tumor, for example, to be used as controls. The kit may also comprise buffers, nucleotide bases, and other compositions to be used in hybridization and/or amplification reactions. Another embodiment of the present invention encompasses a kit for use in detecting a prostate disease state by analysis of a biological sample comprising oligonucleotide probes effective to bind with high affinity to the NELM marker. In a further embodiment, the invention encompasses a kit for use in detecting a prostate disease state by analysis of a biological sample comprising antibodies specific for proteins encoded by the nucleic acid markers of prostate disease identified in the present disclosure.

In a general embodiment, the present invention provides a method for screening a compound for its ability to affect the up-regulation or cause a decrease in the expression of NELM markers. The method comprises the following steps: providing an expression construct comprising NELM-associated promoter and a reporter gene, wherein the reporter gene is under transcriptional control of the promoter, transfecting the mammalian cells with the expression construct, contacting the transfected cell with the compound; and identifying a compound that regulates expression of the reporter gene from the promoter. In a preferred embodiment, the reporter gene is selected from the group consisting of firefly luciferase, chloramphenicol acetyl transferase, beta-galactosidase, green fluorescent protein, human growth hormone, alkaline phosphatase, beta-glucuronidase or any reporter known to those in the art.

Immunogens for raising antibodies to NELM associated products. Many methods to produce antibodies to products are well known to those in the art, and can include antibody production by mixing the antigens encoded by the polynucleotide of the present invention with adjuvants. Alternatively, polypeptides are made as fusion proteins to larger immunogenic proteins, or nucleic acids and peptides can be chemically coupled to large immunogenic proteins such as keyhole limpet hemocyanin. Polypeptides are also covalently linked to other larger immunogenic proteins. Immunogens are typically administered intradermally, subcutaneously, or intramuscularly. Immunogens are administered to experimental animals such as rabbits, sheep, mice, and human volunteers, with adjuvants to generate antibodies. Optionally, the animal spleen cells are isolated and fused with myeloma cells to form hybridomas that secrete monoclonal antibodies. Such methods are well known in the art. According to another method known in the art, the polynucleotide is administered directly, such as by intramuscular injection, and expressed in vivo The expressed protein generates a variety of protein-specific immune responses, including production of antibodies and cell-mediated immune responses, comparable to administration of the protein.

Another embodiment of the present invention is to detect natural antibodies to NELM-associated products in patient samples. Patients expressing the NELM products could produce autoantibodies to these products. As such, any method involving the detection of antibodies to NELM-associated products would be of use in diagnosing disease. For such immunoassays, any type of patient samples can be used, including tissue, organs, cells, urine, saliva, blood, prostatic fluid, or semen.

In addition to the antibodies discussed above, genetically engineered antibody derivatives are made, such as single chain antibodies or humanized antibodies.

4. BRIEF DESCRIPTION OF THE DRAWINGS

For a further understanding of the nature and objects of the present invention, reference should be made to the following detailed description taken in conjunction with the accompanying drawings, in which, like parts are given like reference numerals, and wherein.

5. DETAILED DESCRIPTION OF THE PREFERRED EMBODIMENT

The cloned gene transcript, referred to herein as the Neuroendocrine-like Marker (NELM) extracted from the human prostate cancer cDNA library, and its expression in the prostate gland and other tissues, along with expression products, is being characterized. Our research examined NELM mRNA expression in over 80 archival specimens of human prostate by in situ hybridization histochemistry, suggest that NELM mRNA is exclusively detected in the epithelium, and not the stroma of the prostate; it is primarily present in malignant, and not benign, epithelia; and almost all cases of premalignant intraepithelial neoplasia (PIN) expressed NELM transcript. Moreover, NELM expression in primary prostate tumors increased progressively with increase in their Gleason grade, and most aggressive tumors displayed the highest level of NELM mRNA abundance as assessed by the area and the intensity of the staining. NELM transcript was also expressed by distant metastases of PC. These results strongly suggest that NELM gene expression can be associated with malignant transformation and tumor progression of the prostate, and that NELM can serve as a reliable marker for not only the detection of precancerous and cancerous lesions of the prostate, but also for the severity of the disease. NELM immunoreactivity was also detected in sera of PC patients suggesting that NELM peptide is either secreted or leaked into serum. Our research further indicates that endogenously secreted NELM increases proliferation, invasiveness and tumorigenicity of PC cells.

Expression of NELM Transcript in Primary Prostate Tumor Specimens:

Using cDNA for NELM as a template, a digoxygenin-labeled anti-sense riboprobe was synthesized. This probe was used to perform in situ hybridization histochemistry in over 57 archived, paraffin-preserved PC specimens. These results have shown that NELM transcript was selectively distributed in the epithelium, and not the stroma, of malignant prostate. The transcript was not detected in BPH specimens or in normal epithelia of PC specimens. The NELM transcript was expressed in moderate levels in premalignant intraepithelial neoplasia (PIN), and was strong in invasive carcinomas, significantly intensifying with increase in the Gleason grade. A high degree of correlation was observed when digitized results of NELM mRNA (Area×Intensity) were compared in normal, PIN and PC specimens. Occasionally, NELM mRNA was also localized to ganglions and neuromuscular junctions, consistent with its neuroendocrine origin.

The NELM cDNA was cloned into pcDNA3.1 vector, and the expressed NELM protein was purified by affinity chromatography, and polyclonal rabbit anti-NELM serum was generated. NELM immunoreactivity was selectively localized to epithelia of malignant prostates, and was absent in benign specimens. When added to the cultures of PC3M prostate cancer cell lines, anti-NELM serum attenuated their growth and invasiveness raising a possibility that NELM promotes growth and/or tumorigenicity of prostate cancer cells.

Rabbit anti-NELM serum was used to develop NELM radioimmunoassay and a limited number of serum samples from healthy volunteers and PC patients were analyzed. The sera were also analyzed for PSA levels These initial results have shown that NELM as well as PSA levels were extremely low in a serum sample of a healthy, clinically normal male volunteer. Both, serum NELM and PSA levels were significantly higher in sera of PC patients. However, NELM levels showed significant increase in sera of two PC patients whose PSA levels were in the normal range. These results seem to indicate that NELM can detect "PSA-normal" in a patient population, which often carry aggressive PC with poor prognosis.

Screening of several PC cell lines for the expression of NELM transcript, show that LNCaP cells contained the least abundance of NELM transcripts. In contrast, DU 145, highly invasive PC cell line contained the highest abundance of NELM transcript. PC-3 and PC-3M had intermediate levels of NELM transcript. These results point to the role of NELM in invasive cancer and warrant the use of NELM as a PC marker for the identification of PC patients with metastatic potential.

NELM cDNA was cloned as a result of our research involving the screening of human prostate cancer cDNA library for calcitonin-like peptides (a family of neuroendocrine peptides). The cloned cDNA was short, but was selectively expressed in malignant prostates. The cDNA was sequenced and the sequence was searched for homology with known mRNA sequences in several public and private databases. The cloned cDNA sequence coincides with the human DNA sequence ENST00000341592 (SEQ. No: 1).

The NELM sequence was localized to two exons on chromosome 12. Several homology searches in several databases could not identify any other cDNA sequence with significant homology to NELM cDNA.

The translation of NELM cDNA sequence yielded an ORF of a 44 amino acid peptide. The peptide sequence was inserted for homology search in protein databases. The search yielded a significant homology (63%, 30/47) with an unnamed human protein product. A 20 amino acid segment of NELM peptide exhibited 100% homology with human neuronal thread protein. In addition, NELM peptide also exhibited high homology (23/38, 60%) with human c-myb sequence raising a possibility of its oncogenic role.

Figure 1:
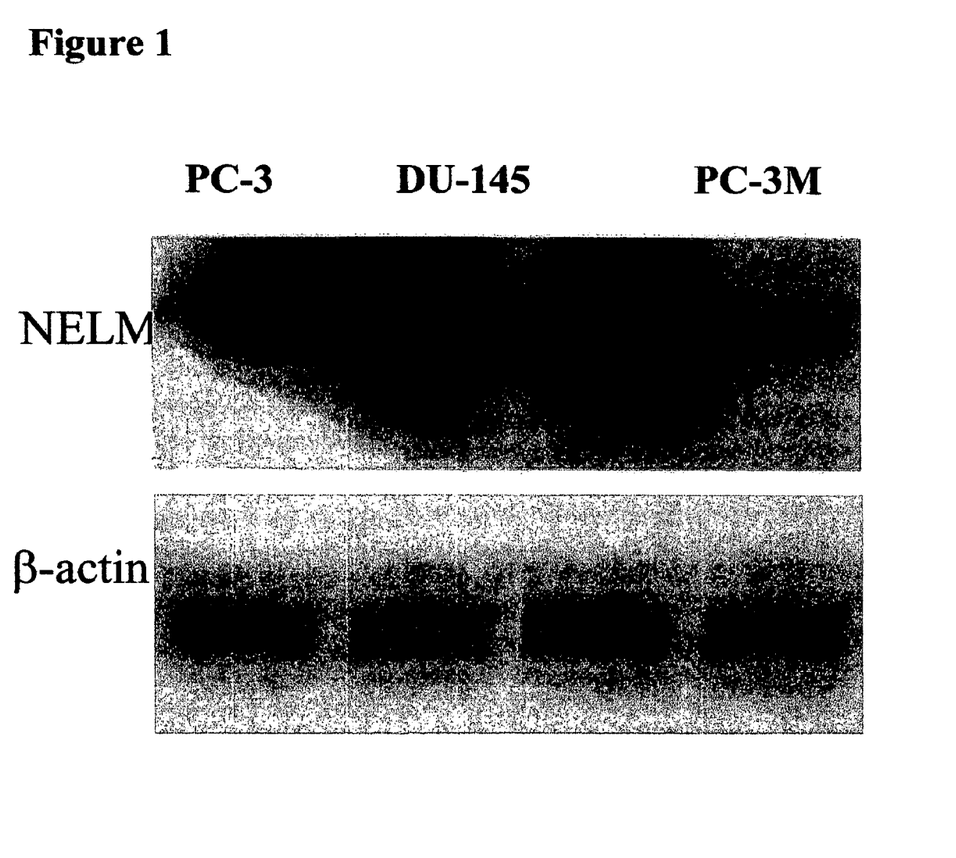
FIG. 1 is a micrograph comparing NELM to β-actin.

In the initial studies, we sought to identify PC cell lines that express NELM transcript. Established PC cell lines such as LNCaP, PC-3, PC-3M and DU-145 were examined. NELM transcript was analyzed by S1-nuclease protection assay. The results presented in FIG. 1 show that: 1) LNCaP cells expressed the lowest abundance of NELM transcript among tested cell lines; 2) the abundance of NELM transcript was in the following order: LNCaP<PC-3<PC-3M</=DU-145.

These results show that: 1) highly invasive, poorly-differentiated DU-145 express the highest level of NELM mRNA; LNCaP, a well-differentiated and indolent cell line, expresses the least amounts of NELM mRNAs; and PC-3 and PC-3M cells, androgen-refractory but not as invasive as DU-145, express NELM mRNA in intermediate abundance. Considering that PC-3M and DU-145 are invasive with high abundance of NELM transcripts, it is conceivable that NELM expression in PC may be indicative of metastasizing potential.

Several primary prostate specimen sections (a total of 78 with BPH and varying grades of PC) were obtained from archived, paraffin-embedded human prostate specimens. The slides were deparaffinized and fixed in 4% paraformaldehyde-PBS (pH 7.2) for 20 minutes, and in situ hybridization immunohistochemistry (ISH) was performed with anti-sense NELM RNA probe as described by Panoskaltis-Mortari and Bucy, 1995. Negative control for the NELM probe was the sense NELM RNA strand.

The cloned NELM cDNA in pGEM vector (Promega, Madison, Wis.) was linearized with either SacII (for antisense strand) or Pst I (for sense strand). The transcription reaction was performed using either SP6 (antisense) or T7 (sense) RNA polymerase in the presence of digoxigenin 11-UTP (Boehringer Mannheim, Indianapolis, Ind.). A riboprobe labeling kit was used and the manufacturer's instructions were followed (Promega). The labeled probes were digested with RNAse-free DNAse (Boehringer), extracted with phenol/chloroform, and purified with TE-microselect D-G50 spin columns (5'-3' Inc., Boulder, Colo.).

Figure 2:
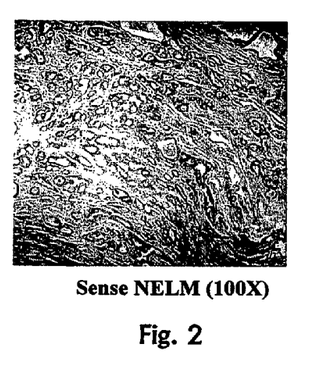
FIG. 2 is a micrograph showing a Prostate Cancer specimen treated with the NELM probe.
Figures 2A, 3:
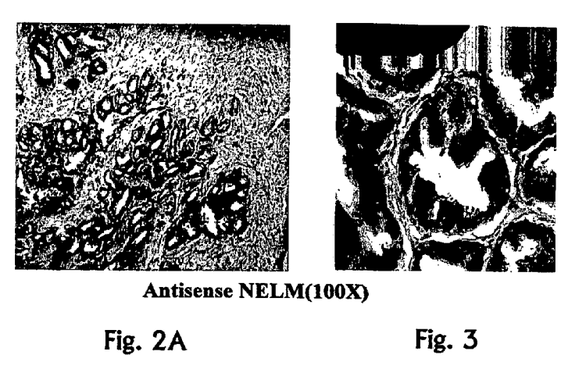
FIG. 2A is a micrograph showing a Prostate Cancer specimen treated with anti-sense NELM probe.
FIG. 3 is a micrograph showing the localization of the NELM transcript in prostate cells.

PC specimens were treated with either sense NELM probe seen in FIG. 2 or anti-sense NELM probe seen in FIG. 2A. As expected, only anti-sense, but not sense, NELM probe identified NELM transcript as indicated by brown stain.

NELM mRNA is selectively localized to epithelial, and not stromal, compartment of the prostate: As depicted in FIG. 3, NELM transcript was exclusively localized to epithelial compartment, and stromal compartment was devoid of this transcript. Considering that PC is epithelial disease, these results again suggest the association of NELM expression and malignant transformation.

Figure 4:
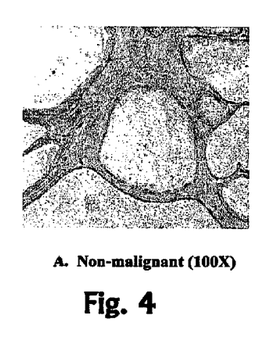
FIG. 4 is a micrograph showing no presence of NELM transcript in BPH specimens.
Figure 4A:
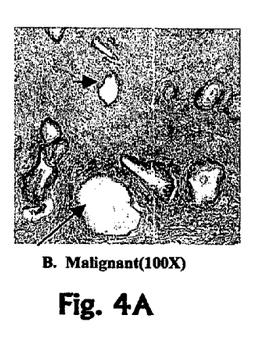
FIG. 4A is a micrograph showing the presence of NELM transcript in malignant epithelia.

NELM transcript was not detected in BPH or normal epithelia of PC specimens depicted in FIG. 4. However, it was present in the malignant epithelia FIG. 4A.

Figure 5:
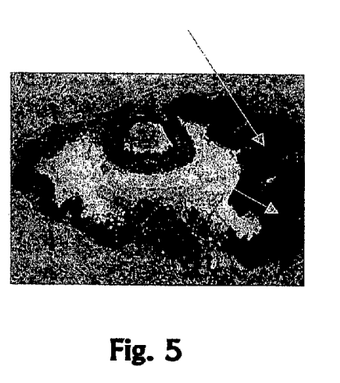
FIG. 5 is a micrograph showing NELM presence in premalignant Prostate cells.

NELM transcript was detected in very early stages of PC such as premalignant intraepithelial neoplasia, which is indicated by heterogeneous staining on right side of FIG. 5.

Figure 6:
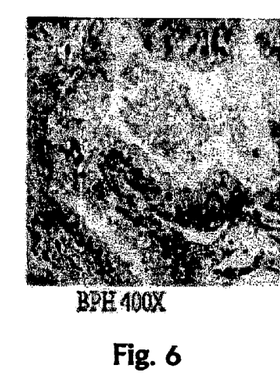
FIG. 6 is a micrograph showing typical NELM expression in BPH prostate cells @ 400×
Figure 6A:
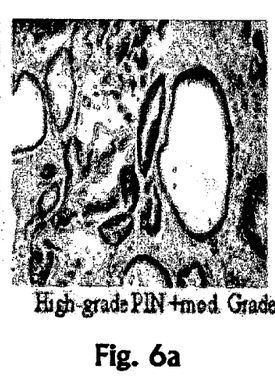
FIG. 6A is a micrograph showing typical NELM expression in high-grade PIN+Moderate Grade cells.
Figure 6B:
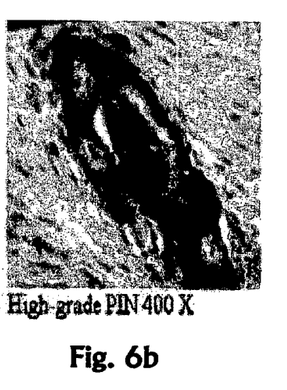
FIG. 6B is a micrograph showing typical NELM expression in High-Grade PIN cells @ 400×.
Figure 6C:
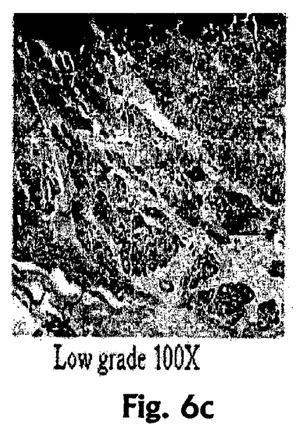
FIG. 6C is a micrograph showing typical NELM expression in Low-Grade cells @100×.
Figure 6D:
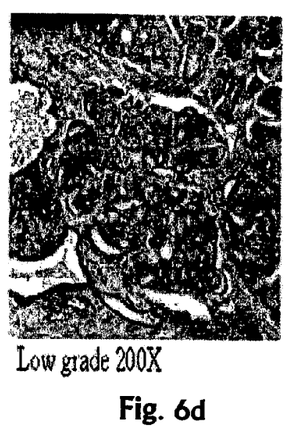
FIG. 6D is a micrograph showing typical NELM expression in Low-Grade cells @ 400×.
Figure 6E:
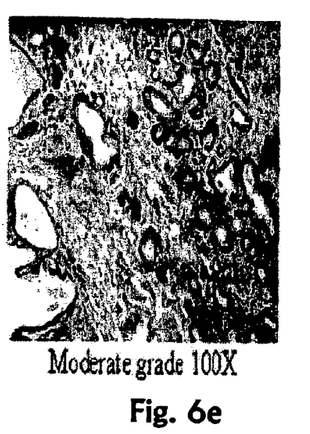
FIG. 6E is a micrograph showing typical NELM expression in Moderate-Grade cells @ 100×.
Figure 6F:
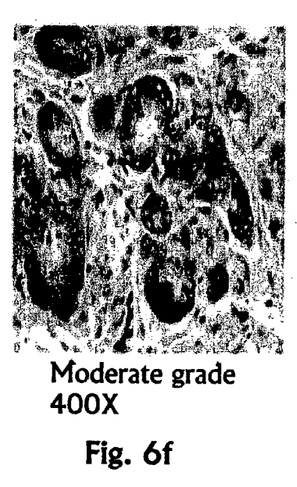
FIG. 6F is a micrograph showing typical NELM expression in Moderate-Grade cells @ 400×.
Figure 6G:
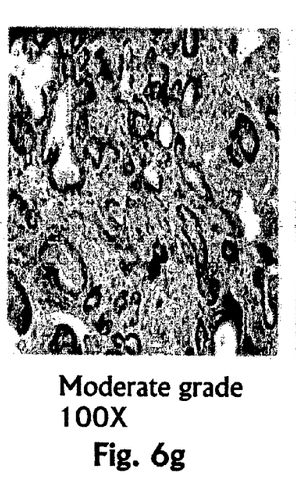
FIG. 6G is a micrograph showing typical NELM expression in Moderate-Grade cells @ 100×.
Figure 6H:
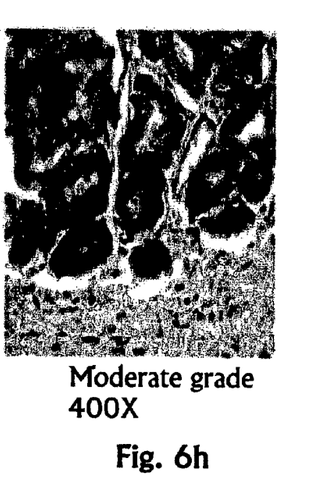
FIG. 6H is a micrograph showing typical NELM expression in Moderate high-Grade cells @ 400×.

Area as well as intensity of NELM mRNA staining increases with increase in tumor grade: Please see the micrographs presented in FIGS. 6 through 6H. These specimens were obtained from a variety of prostate tissues and represent typical NELM expression in cases ranging from BPH (the lowest level of expression) to moderate high grade PC (most intense expression among the tissues presented here). Especially important was the significant NELM transcript expression in cases of PIN.

Correlation between NELM mRNA expression and tumor grade: NELM specimens staining of PC were quantified (area×intensity) by image analysis of digital micrographs. The area and intensity were digitized by particle analysis using Image J image analysis program. The digitized data was then statistically evaluated by One Way Analysis of variance, and significance was derived from Newman-Keuls test. Benign Acini PIN Acini Carcinoma (Gleason: 1-6) Carcinoma (Gleason: 7-10) Number of cases 23 11 21 23 Mean±SEM 13.51±3.01 39.73±3.17*47.13±4.95*93.25±3.83*significantly different from benign acini ($p<0.05$)significantly different from benign and PIN acini ($p<0.05$)

Figure 7:
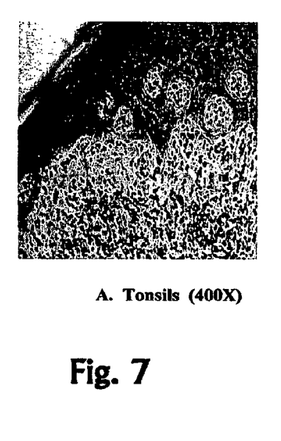
FIG. 7 is a micrograph showing a tonsil specimen as a control.
Figure 7A:
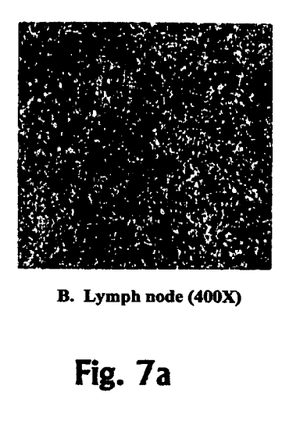
FIG. 7A is a micrograph showing NELM presence in lymph node specimen.
Figure 7B:
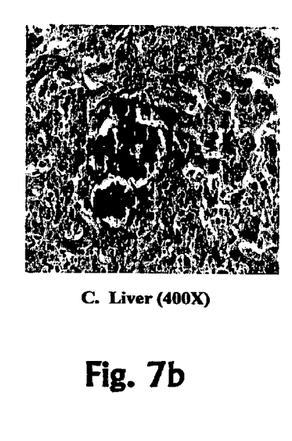
FIG. 7B is a micrograph showing NELM presence in a liver specimen.

FIGS. 7-7B presents typical micrographs of NELM mRNA expression in lymph node and liver metastases of PC. Tonsil FIG. 7 specimen was used as a negative control and did not exhibit any NELM mRNA expression. In contrast, NELM expression was intense in lymph node shown in FIG. 7A and in the liver FIG. 7B. However, host cells did not express any NELM transcripts.

Preparation of anti-NELM rabbit serum was prepared by immunizing rabbits with NELM-KLH conjugate according to standard procedure in Freund's complete adjuvant. Booster doses were given in Freund's incomplete adjuvant. The rabbits were bled ten days after the third booster injection and antibody NELM production was monitored by enzyme-linked immunosorbant assay using NELM as the antigen. The antiserum was then tested for cross-reactivity with several neuropeptides including calcitonin, CGRP, vasoactive intestinal peptide, PACAP, neuropeptide Y, vasopressin etc. The antiserum did not cross react with either of these peptides.

Figure 8:
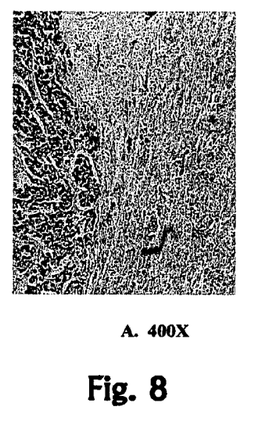
FIG. 8 is a micrograph showing no rabbit anti-NELM serum staining in stroma cells.
Figure 8A:
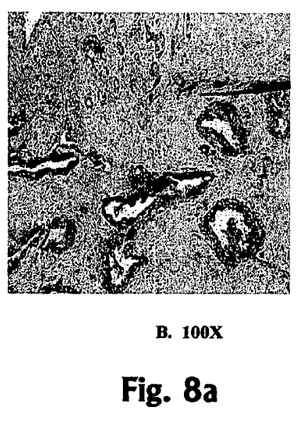
FIG. 8A is a micrograph showing presence rabbit anti-NELM serum staining in epithelial cells.
Figure 8B:
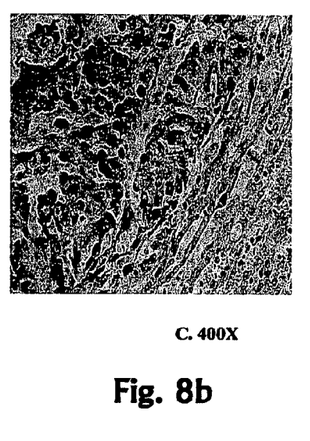
FIG. 8B is a micrograph showing presence rabbit anti-NELM serum staining in epithelial cells.

FIGS. 8-8B presents NELM immunohistological staining in PC specimens using rabbit anti-NELM serum. The antiserum was specific, and NELM antigen was selectively localized to the epithelial compartment, as seen in FIGS. 8A and 8B with no staining in stroma, as seen in FIG. 8. These results are consistent with those observed in NELM hybridization histochemistry, and again demonstrate specificity of the antiserum.

Figure 9:
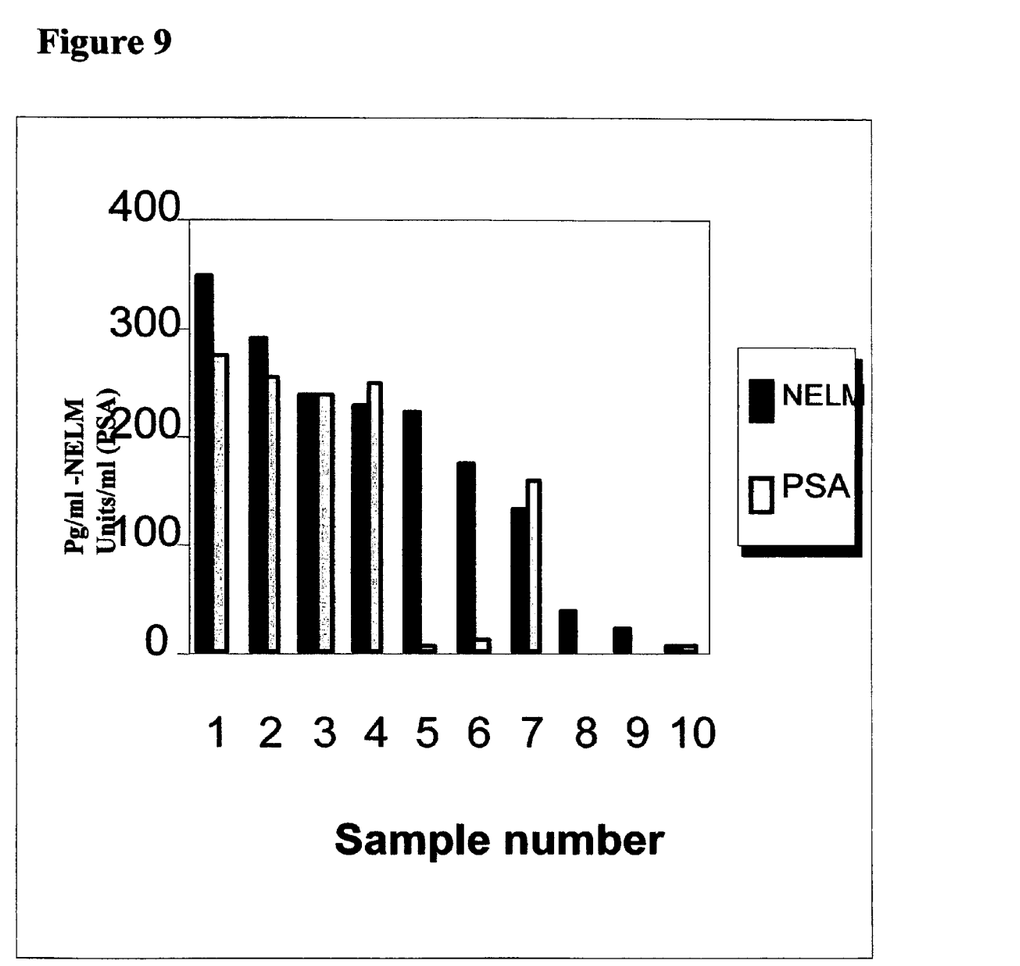
FIG. 9 is a chart comparing PSA and NELM values for same samples.

A radioimmunoassay for NELM was set up using rabbit anti-NELM serum. NELM antigen was iodinated with 125I-NaI by chloramine T method, and uniodinated NELM was used as standard reference preparation. The assay used non-equilibrium method, and serum samples had to be deproteinized using TCA/Ethanol-Acetic acid precipitation method. The sensitivity of the assay was 40 pg/ml, and variation between assays was <9%. Serum samples were from patients as well as normal, male volunteers. Ten samples had sufficient volumes to repeat the assay twice, and were therefore, analyzed. The results presented in FIG. 9 provide PSA and NELM values in same samples. PSA levels of these samples ranged from 23-2046 units/ml. Sample #10 was from a healthy, normal male volunteer, and the serum NELM as well as PSA levels were barely in detectable range. Samples #1-9 were from PC patients at various stages of the disease. For example, sample #8 and 9 were from BPH cases whereas #5-6 were from patients with aggressive PC. It is interesting to note that NELM in samples 5-6 were high although PSA was very low. This is because these patients had clinical cancer, which could not be detected by serum PSA test. In addition, serum NELM was higher in #8-9, where PSA was undetectable. It remains to be seen if these patients were cases of pure BPH or also had premalignant intraepithelial neoplasia (PIN) lesions. Overall, a good correlation between serum NELM and PSA was observed ($r=0.692$). These results support the possibility that NELM may detect cases of PC with "normal PSA".

NELM Function.

Experiments were conducted to identify a possible function of NELM in prostate pathophysiology. Since NELM expression was very high in tumors and PC cell lines with metastatic potential, we tested the effect of anti-NELM serum on invasion activity of DU-145 cells.

These experiments were conducted in 6 well, two compartmented, Matrigel invasion chambers (Becton Dickinson, Bedford, Mass.). 200,000 DU-145 cells were suspended in 500 µl RPMI 1640 medium (containing 0.1% BSA, 10 mM HEPES, 4 mM L-glutamine, 100 IU/ml penicillin G and 100 ug/ml streptomycin), and seeded in the upper compartment of the invasion chamber. The lower chamber received the chemo attractant medium, which consisted of 80% complete medium and 20% conditioned medium from the cultures of DU-145 cells expressing constitutively active G□protein (Glinski et al, 2004). Various concentrations of rabbit anti-NELM serum were added in the lower chamber. Appropriate amounts of non-immune rabbit serum were added to keep the total amount of serum constant in all experimental groups. The incubations were carried out for 24 hours. At the end of this period, the matrix gel was scraped off using cotton swabs, and the top insert was fixed and stained using Diff Quick Staining (Dade Diagnostics, Aguada, PR). The number of cells migrated on the outer bottom side of the upper invasion chamber were counted under the microscope (magnification: 100×). At least twenty randomly selected fields were examined, and the final results were expressed as relative invasion, where the number invading cells in vehicle control were considered as 1, and those in treated groups were presented with reference to the control.

As DU-145 cells exhibit high growth rates, it is likely that the cells migrated during early part of 24 hour incubation period could proliferate during the course of the experiment. This could possibly lead to overestimation of the final results. To correct this probability, we determined the growth rate of Du-145 cells under identical culture conditions. 100,000 DU-145 cells were plated in six-well dishes and cultured in the chemo attractant medium for 24 hours. The increase in the cell number was determined, and this correction was applied to the results of invasion assay.

Figure 10:
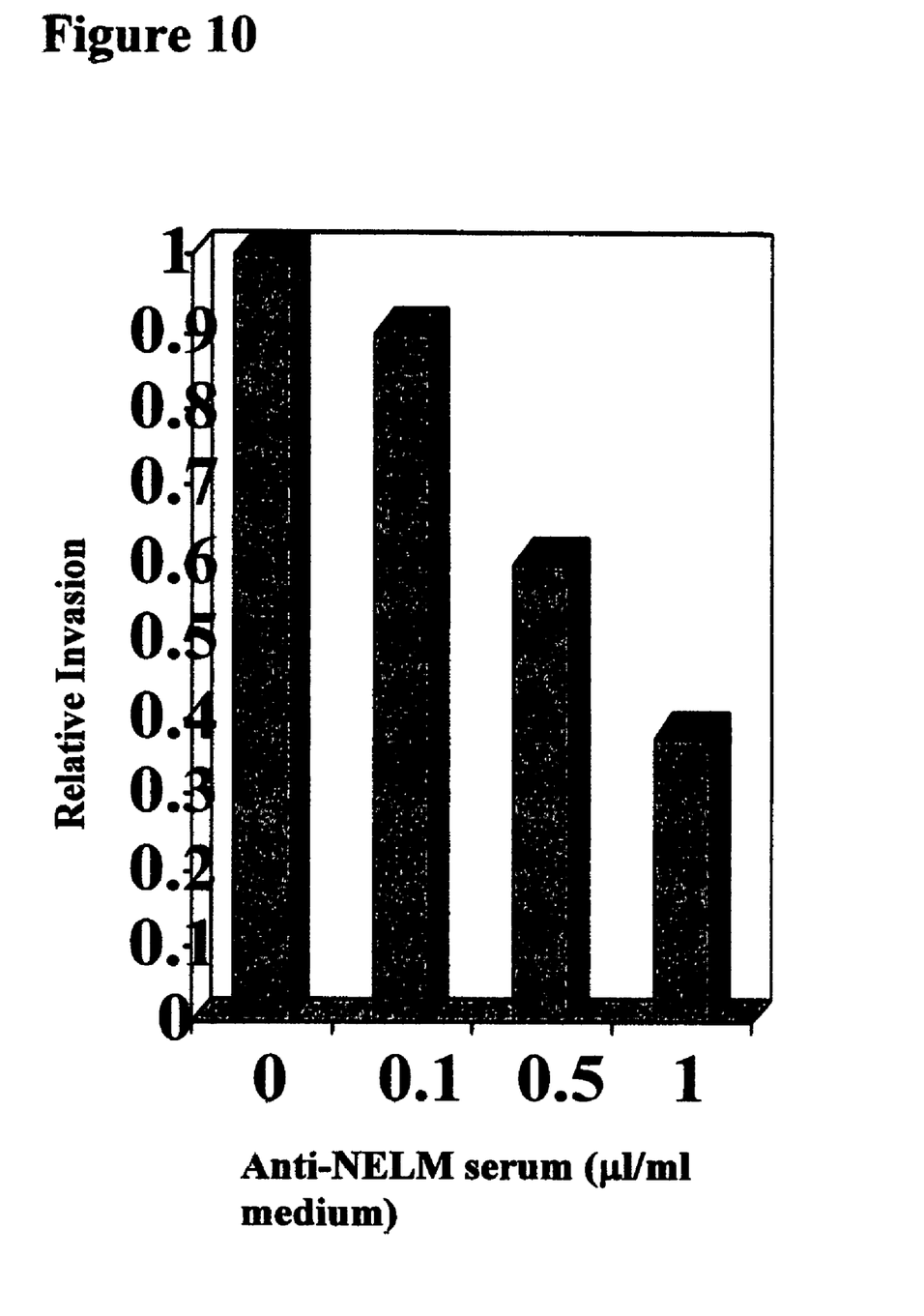
FIG. 10 is a chart showing invasiveness of DU-145 relative to dosage.

The results presented in FIG. 10 suggest that anti-NELM serum reduced invasiveness of DU-145 cells in a dose-dependent manner, and raised a possibility that NELM may be associated with metastasis of prostate cancer.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in any limiting sense.

What is claimed is:

1. A method for detecting prostate cancer in a patient using a neuroendocrine-like marker derived from the polynucleotide sequence set forth as SEQ ID NO: 1 comprising the steps of:
   a) obtaining one or more test samples from prostate tissue or serum of said patient;
   b) detecting the expression of one or more markers selected from the group consisting of:
      i. the polynucleotide sequence set forth as SEQ ID NO: 1;
      ii. the complement of the polynucleotide sequence set forth as SEQ ID NO: 1; and
      iii. a protein translated from the polynucleotide sequence set forth as SEQ ID NO: 1;
   c) detecting an increase of said one or more markers in said test samples over a level of said one or more markers found in an individual without prostate cancer, wherein said increase in said one of more markers indicates the presence of prostate cancer in said patient.

2. The method of claim 1 wherein said prostate tissue sample comprises epithelial tissue.

3. The method of claim 1 wherein said marker is mRNA transcribed from the polynucleotide sequence set forth as SEQ ID NO: 1.

* * * * *